US012580070B2

(12) United States Patent
Atanasiu

(10) Patent No.: US 12,580,070 B2
(45) Date of Patent: Mar. 17, 2026

(54) SYSTEMS, METHODS, AND DEVICES FOR INDEXING AND SEARCHING DIGITAL IMAGING AND COMMUNICATIONS IN MEDICINE (DICOM) METADATA

(71) Applicant: Hyland Software, Inc., Westlake, OH (US)

(72) Inventor: Razvan Atanasiu, Westlake, OH (US)

(73) Assignee: Hyland Software, Inc., Westlake, OH (US)

( * ) Notice: Subject to any disclaimer, the term of this patent is extended or adjusted under 35 U.S.C. 154(b) by 382 days.

(21) Appl. No.: 18/308,770

(22) Filed: Apr. 28, 2023

(65) Prior Publication Data

US 2024/0363229 A1     Oct. 31, 2024

(51) Int. Cl.
| | |
|---|---|
| *G16H 30/20* | (2018.01) |
| *G06F 16/51* | (2019.01) |
| *G06F 16/58* | (2019.01) |
| *G16H 50/70* | (2018.01) |

(52) U.S. Cl.
CPC ............. *G16H 30/20* (2018.01); *G06F 16/51* (2019.01); *G06F 16/5866* (2019.01); *G16H 50/70* (2018.01)

(58) Field of Classification Search
None
See application file for complete search history.

(56) References Cited

U.S. PATENT DOCUMENTS

| | | | | | |
|---|---|---|---|---|---|
| 2002/0016718 | A1* | 2/2002 | Rothschild | ............. | G16H 30/20 |
| | | | | | 705/2 |
| 2007/0118540 | A1 | 5/2007 | Guo | | |

| | | | | | |
|---|---|---|---|---|---|
| 2010/0049740 | A1* | 2/2010 | Iwase | ..................... | G16H 10/60 |
| | | | | | 705/7.27 |
| 2011/0110568 | A1* | 5/2011 | Vesper | ................... | G06Q 10/10 |
| | | | | | 382/128 |
| 2015/0081846 | A1 | 3/2015 | Ur-Rahman et al. | | |
| 2021/0265041 | A1* | 8/2021 | Narayanan | ............. | G16H 30/20 |

FOREIGN PATENT DOCUMENTS

| | | |
|---|---|---|
| JP | 2015529874 A | 10/2015 |
| KR | 1020220146310 A | 11/2022 |
| KR | 1020230009564 A | 1/2023 |

OTHER PUBLICATIONS

Search Report dated Aug. 5, 2024 in connection with PCT Application No. PCT/US2024/024189.
Written Opinion dated Aug. 5, 2024 in connection with PCT Application No. PCT/US2024/024189.

* cited by examiner

*Primary Examiner* — Thomas D Lee

(74) *Attorney, Agent, or Firm* — Eschweiler & Potashnik, LLC

(57) ABSTRACT

Techniques, described herein, enable enhanced indexing and searching of digital imaging and communications in medicine (DICOM) systems and records. Upon receiving DICOM objects in one or more DICOM studies via an interface to medical modalities, DICOM metadata can be extracted from the DICOM object headers of the DICOM objects. DICOM values of DICOM tags from the DICOM object headers can be indexed to enable a relational database or a non-structural queried language (non-SQL) database to be searchable for each value of the DICOM tags. Additional features of the techniques are described herein.

20 Claims, 9 Drawing Sheets

300

RECEIVE STUDY BATCH AND RETRIEVE DICOM OBJECTS FOR STUDY BATCH ⌐ 310

EXTRACT DICOM METADATA FROM DICOM OBJECT HEADERS OF DICOM OBJECTS ⌐ 320

INDEX DICOM VALUES OF DICOM TAGS FROM THE DICOM METADATA TO ENABLE SEARCHING FOR RELATED MEDICAL INFORMATION IN A REALATIONAL DATABASE OR NON-SQL DATABASE ⌐ 330

800

RECEIVE STUDY BATCH AND RETRIEVE DICOM OBJECTS FOR STUDY BATCH — 810

EXTRACT DICOM METADATA FROM DICOM OBJECT HEADERS OF THE DICOM OBJECTS — 820

INDEX DICOM VALUES OF DICOM TAGS FROM THE DICOM OBJECT HEADERS TO ENABLE A RELATIONAL DATABASE OR A NON-SQL DATABASE TO BE SEARCHABLE FOR EACH VALUE OF THE DICOM TAGS — 830

SYSTEMS, METHODS, AND DEVICES FOR INDEXING AND SEARCHING DIGITAL IMAGING AND COMMUNICATIONS IN MEDICINE (DICOM) METADATA

FIELD

This disclosure relates to indexing and searching of digital imaging and communications in medicine (DICOM) meta-data.

BACKGROUND

Computerized networks and data management systems can include a variety of systems, devices, and technologies to enable users to create, store, access, and distribute infor-mation. Such networks can include one or more wired networks, wireless networks, or a combination thereof. Each network can include a broad range of interconnected devices, each comprising hardware, software, virtualization technology, etc., which enables the devices to send, receive, process, and/or store information. Examples of such devices can include mobile user devices (e.g., cell phones, tablet computers, laptop computers, etc.) stationary devices (e.g., desktop computer, servers, etc.), and network components and devices (e.g., network hubs, routers, base stations, satellite systems, etc.).

Digital imaging and communications in medicine (DI-COM) is a standard used for the communication and man-agement of medical imaging information and related data. DICOM can be used by, for example, hospitals, doctor offices, government agencies, research institutions, and other types of organizations. DICOM can be implemented for storing and transmitting medical images, enabling the integration of medical imaging devices such as scanners, servers, workstations, printers, network hardware, and pic-ture archiving and communication systems (PACS) from multiple manufacturers.

BRIEF DESCRIPTION OF THE DRAWINGS

The present disclosure will be readily understood and enabled by the detailed description and accompanying fig-ures of the drawings. Like reference numerals can designate like features and structural elements. Figures and corre-sponding descriptions are provided as non-limiting examples of aspects, implementations, etc., of the present disclosure, and references to "an" or "one" aspect, imple-mentation, etc., can not necessarily refer to the same aspect, implementation, etc., and can mean at least one, one or more, etc.

DETAILED DESCRIPTION

Figure 1:
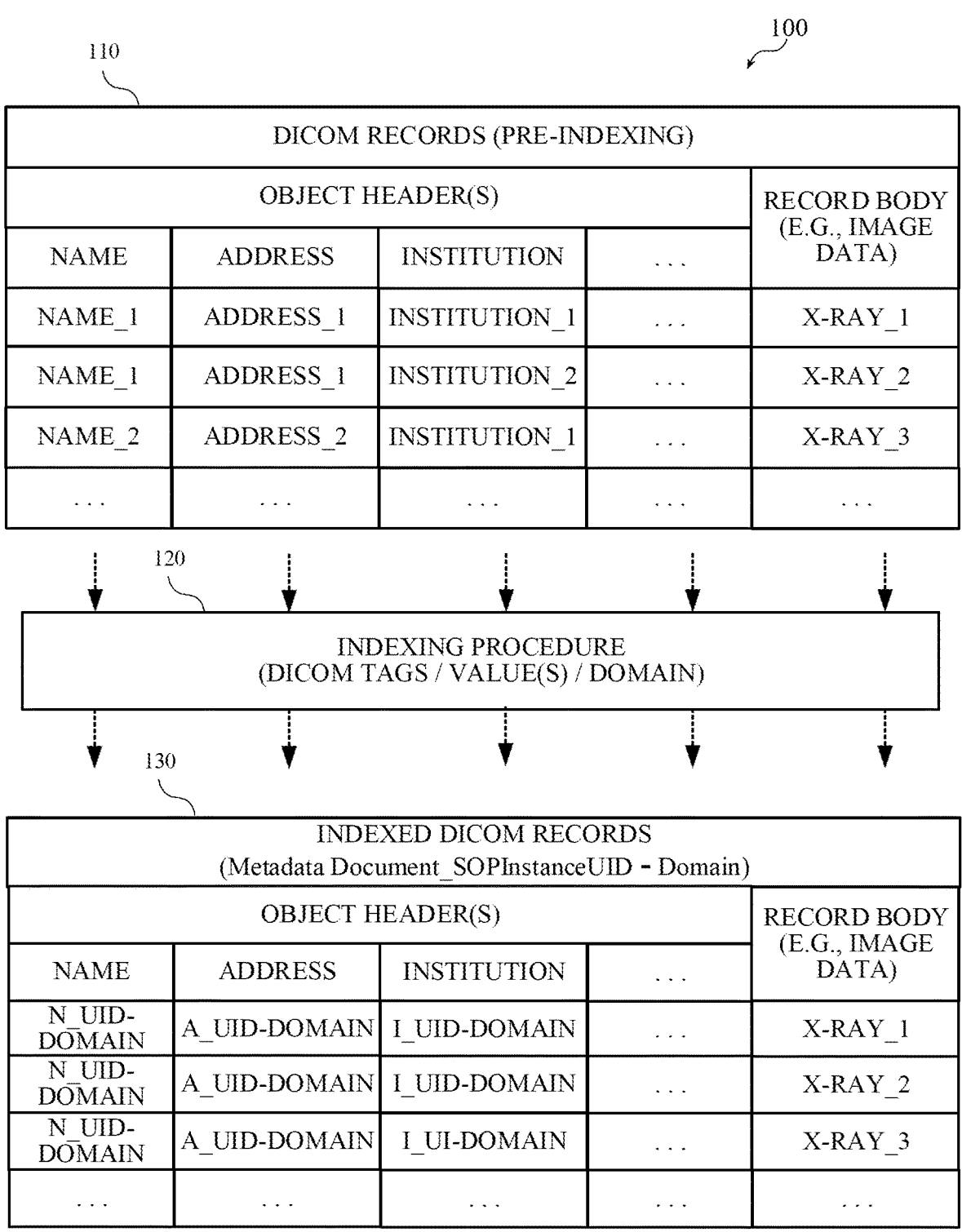
FIG. 1 is a diagram of an example overview according to one or more implementations (aspects) described herein.

The following detailed description refers to the accom-panying drawings. Like reference numbers in different drawings can identify the same or similar features, elements, operations, etc. Additionally, the present disclosure is not limited to the following description as other implementa-tions can be utilized, and structural or logical changes made, without departing from the scope of the present disclosure.

The digital imaging and communications in medicine (DICOM) standard describes a format of medical images, as well as their distribution, in terms of a communication protocol. The information model for DICOM can include one to many relationships between main information entity levels, which include a patient, a study, a series and an instance/image, in which a core unit is an imaging study. Each DICOM instance or DICOM object can be in a binary format and can consist of a header, which can include a dictionary of key value pairs. A key can also be referred to as a DICOM tag that are associated with a DICOM diction-ary of tags. A tag can also have a value representation (VR) type or code, such as a PN (person name), UI (unique identifier), SH (short string), LO (long string), OB (binary data), etc.

An aspect of DICOM systems can include indexing and searching operations of DICOM metadata, whereby medical records of a DICOM study formatted according to the DICOM standard can be indexed by extracting metadata from the header of each DICOM object in order to properly persist the medical studies, as well as support radiology and other medical study (multi-ology) workflows. In particular, a clinician can direct viewable studies across volumes of metadata for analysis and analytics in an efficient and simplified manner of performing medical studies according to enhanced indexing and searching operation.

A server device or system can operate to receive medical information such as DICOM objects from one or more medical modalities (e.g., radiography (X-ray) machines, computed tomography (CT) scanners, magnetic resonance imaging (MRI) machines, positron emission tomography (PET) scanner, or other medical equipment) via an interface. The interface can be a wide area network (WAN), a local area network (LAN), a metropolitan area network (MAN), an ad hoc network, an intranet, the Internet, a virtual network (e.g., a virtual private network (VPN)), a telephone network (e.g., a Public Switched Telephone Network (PSTN)), a Voice over IP (VOIP) network, or a combination of these or other types of interface(s) or network(s). Meta-data can be extracted from each DICOM object header of the DICOM objects of a DICOM study or batches of DICOM studies so that all of the metadata can be indexed, each value of each tag of each DICOM object header of each DICOM object/instance. In particular, the DICOM values of DICOM tags from the DICOM object headers can be indexed to a relational database or a non-structural queried language (non-SQL) database to be searchable for each value of the DICOM tags within one or more DICOM studies.

Generally, a DICOM medical record or file can include a header and a body arranged according to a format specified by the DICOM standards. The header can include a variety of attributes (also referred to as keys, tags, DICOM tags, etc.), some of which can be identifying information. The body can include, for example, the imaging information of the corresponding x-ray, MRI, etc., which can also include pixel data as a part of DICOM metadata. However, each and every DICOM metadata and associated values/tags are not usually entirely indexed in a relational database or a non-structural queried language (non-SQL) database. Indexing and searching operations herein can include every value of every tag in every one of the DICOM headers of every DICOM object of every medical imaging study or DICOM study to be associated with a relational database or a non-SQL database, where implementations/aspects herein enable simplified searching of the indexed DICOM metadata.

The quantity of records to be indexed and searched in a given batch or set of medical records/DICOM studies can be large and complex (e.g., involving up to or more than millions of records, multiple studies, across multiple institutions, etc.). Each DICOM study or medical study can involve one or more various modality inputs and outputs of DICOM objects as well as past and present cross-discipline studies on a patient, patient identification (ID) a particular health record, a timeline, medical specialty, medical enterprise, topic, etc., that can span a patient a study, a series, an instance, other attribute/information entity level or the like. Each DICOM medical study can be composed of discrete DICOM instances or objects. As such, an ability to index entire sets/batches/volumes of medical records in studies efficiently is desirable so that indexing can be performed for every value of every tag of every header of every DICOM object of every medical imaging study in a vendor neutral archive (VNA). Subsequently, this data can be available for search operations and analytics based on analytics of all values.

A DICOM platform, server system or device can perform archiving and distribution of medical studies with visualization that is unique to various searching engines based on the DICOM indexing of DICOM metadata, in which the acquisition and any associated medical images are grouped. Most DICOM instances or objects can include pixel data for DICOM images, but not necessarily, in which some may not, but each DICOM instance or objects have a DICOM header with associated DICOM metadata. For example, a magnetic resonance (MR) or computerized tomography (CT) imaging patient study can have multiple or multi-modal MRI/CT scans for imaging that has up to or more than thousands of slices sent independently from one or more modalities to the medical databases. Grouping of the batches can be done based on the DICOM metadata because the batches of medical DICOM studies can all have the same metadata that aggregates at the study level or series level among a hierarch of information entity levels. Each study can have multiple DICOM instances or objects, in which one or more medical exams from modalities can be accumulated based on one or more physical patients. The server can extract the metadata from all of the DICOM objects and index them with addition application programming interfacing (API) for data mining, which can be for a specific modality, or multiple modalities (e.g., Chest X-rays, or other imaging scan) spanning different modality types (CT, MRI, X-ray, etc.) or the same modality type. Alternatively, or additionally, a population research study could be performed based on a particular population or time range from the indexed DICOM metadata for a cross-sectional study of population or at the hospital/institution, geography, patient(s), or otherwise. Techniques, described herein, enable enhanced DICOM indexing and searching solutions for efficient analysis.

FIG. 1 is a diagram of an example overview 100 according to one or more aspects described herein. As shown, overview 100 can include pre-indexed DICOM study records 110 with DICOM objects of a medical study, an indexing procedure or component 120, and indexed DICOM records 130. As described herein, a set (i.e., one or more) of DICOM studies/records can be referred to as a DICOM batch or study, and a DICOM record can be referred to as a DICOM object or instance. Referring to FIG. 1, each pre-indexed DICOM record 110 can include a record or DICOM object header that includes one or more tags or attributes and a record body. Examples of tags can include patient name (e.g., NAME_1, NAME_2, etc.), patient address (e.g., ADDRESS_1, ADDRESS_2, etc.), institution name (e.g., INSTITUTION_1, INSTITUTION_2, etc.), or other tags. An example of a record or object body can include image or pixel data (e.g., X-RAY_1, X-RAY_2, etc.).

The information entity model in DICOM includes one to many relationships from one level to the next in an information entity hierarchy, or between main information entity levels that include the following: patient level, study level, series level, and instance/image level. A patient for example can have multiple studies, while multiple studies can comprise multiple series of different DICOM instances/objects. A DICOM study, which belongs to a patient is a collection of DICOM instances. Each DICOM instance contains business keys that allow a DICOM study to be assembled from the DICOM instances header information. The business keys typically used are issuer of patient ID and patient ID (or medical record number (MRN)) at a patient level, a study instance unique ID (UID) (studyinstanceUID) at a medical study level, a series instance UID (seriesinstanceUID) at a series level, and a DICOM service object pair (SOP) instance UID (SOPInstanceUID) at a DICOM instance level. The studyUID, seriesUID and SOPInstanceUID are type 1 tags, have to be present, have an associated value and are of type UID tags. A patient ID (PatientID)/MRN are type 2 tags, while usually present, they do not necessarily have a value according to the DICOM standard. Other important tags can be used in association with a DICOM object as business keys also.

DICOM applications can use variable combinations of these tags to define uniqueness across information entity levels, and therefore establish the proper information object hierarchy, which is constructed from disparate DICOM instances. At the patient level, the patient name tag can be used, as well as patient's sex and birthdate. In radiology, the accession number tag value can be important for interpretation of workflows and billing. There are also several DA (date), TM (time) and DT (date time) type of tags, for example, for a study date association with searching of the indexed DICOM metadata.

Indexing all metadata of a large number of medical imaging studies that typically can go back more than 20 years can be an analytics treasure trove. Use cases vary from efficiency key performance indicators (KPIs) of modality acquisition and diagnostic reading to population health research, for example. Pre-indexed DICOM records 110 can be subjected to an indexing procedure 120. As described herein, aspects include applying extractions of DICOM metadata from the DICOM instances and offering additional APIs associated with the indexed DICOM metadata, which can include the tags being associated with values of business keys to DICOM tags/value representation, or other tags.

The indexing 120 can comprise generating a metadata document from the DICOM object headers as a JavaScript object notation (JSON) metadata document or an extensible markup language (XML) metadata document from the DICOM object headers. Specifically, the indexing 120 can include generating the JSON or XML metadata document from the DICOM values associated with DICOM tags from the DICOM object headers via various correlations.

In an aspect, the JSON (or XML) metadata document can be generated at the DICOM object/SOPInstanceUID level from among the different information entity levels (patient, study, series, instance), rather than at the DICOM study level, which would have been an aggregation of DICOM object headers. The key or business key that can be used for a metadata document as this can be a concatenation of the SOPInstanceUID (e.g., illustrated in FIG. 1 as UID) and the domain (e.g., the Issuer of PatientID/Application Source/ Tenant) separated by '-'. Thus, metadata can be indexed and searched according to the SOPInstanceUID, the domain or both. The domain can refer to a location of an associated database as a sub-set of an institution or tenant, where the tenant refers to one or more DICOM databases within or across a medical enterprise/entity. An example, search string to acquire an indexed object header, value or tag of DICOM metadata could be as follows: document/ 1.2.840.113619.2.30.1.1762288588.1465.911090938.270-DICOMDB1. The metadata document (e.g., JSON metadata document/XML metadata document) can be indexed at the DICOM instance level of information entity levels according to a SOPInstanceUID and a Domain, as a business key and value representation in combination or concatenation, rather than at the record or study level, with an aggregation of various object headers.

In response to DICOM metadata being indexed based on a metadata document and a combination of keys, various APIs can be leveraged for metadata indexing 120. The value of this approach as a whole, is the availability of an end-to-end solution within medical institutions. In addition to archiving tens of millions of DICOM studies, the entire metadata of the DICOM object headers can be indexed and available for analytics and DaaS (data as a service) initiatives. This can be done at scale without significant tradeoffs in performance. Search and analytics results can be then easily converted to clinical actions, for example, launching a diagnostic viewer on a specific DICOM study as part of a result.

Figure 2:
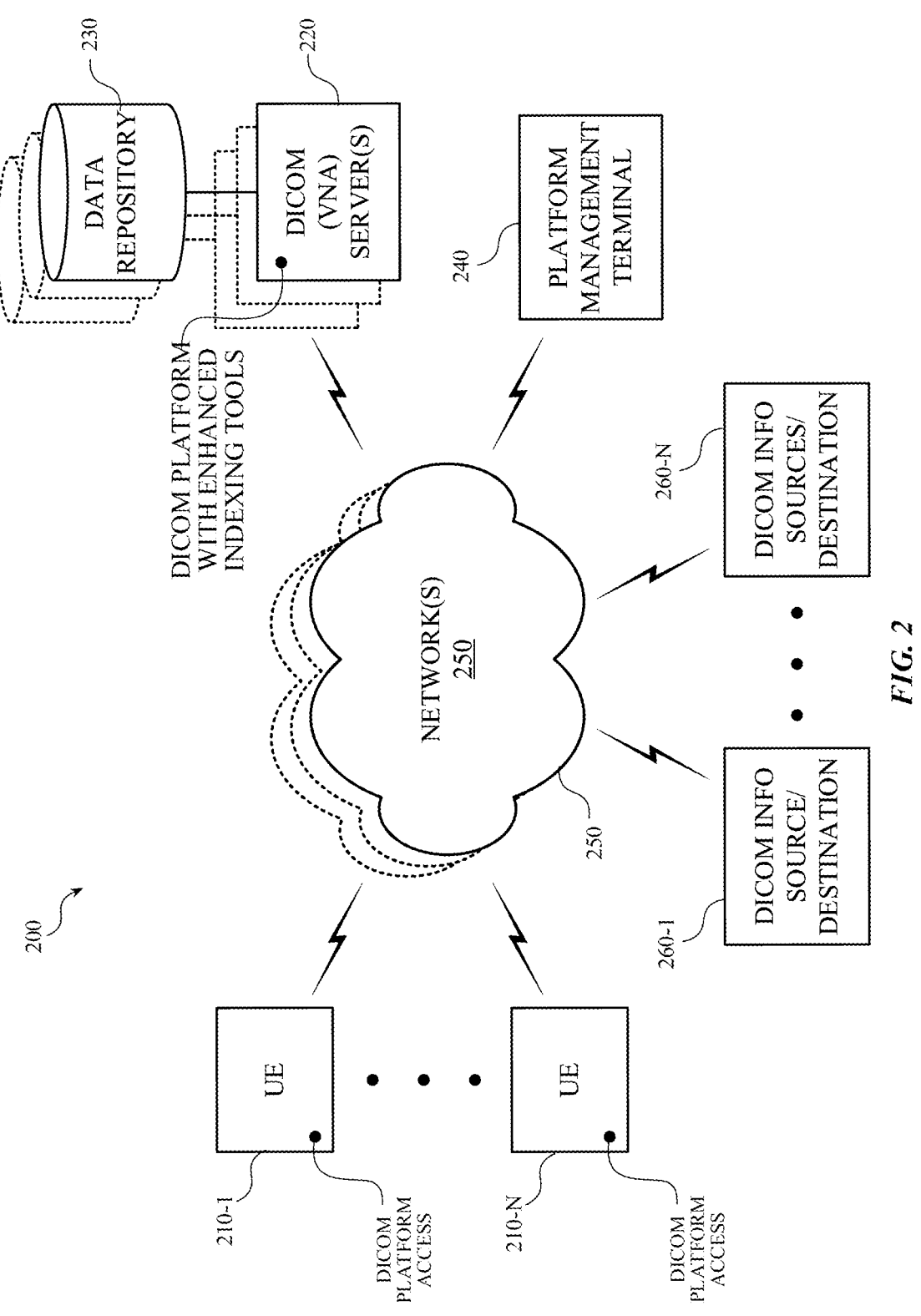
FIG. 2 is a diagram of an example network according to one or more implementations described herein.

FIG. 2 is a diagram of an example environment 200 in which systems or methods, described herein, can be implemented. As depicted, environment 200 can include user equipment (UE) as medical modalities 210-1, . . . 210-N (where N is greater than or equal to 2 and collectively referred to as "UEs 210"), DICOM servers 220, data repositories 230, platform management terminal 240, DICOM source/destination 250-1, . . . 250-M (where N is greater than or equal to 2 and collectively referred to as "DICOM sources/destinations 250"), and network 250. The number of devices and/or network, illustrated in FIG. 2, is provided for explanatory purposes only. In practice, there can be additional devices and/or networks, fewer devices and/or networks, different devices and/or networks, or differently arranged devices and/or networks than illustrated in FIG. 2. Devices of environment 200 can interconnect via wired connections, wireless connections, or a combination of wired and wireless connections. Also, in some implementations, one or more of the devices of environment 200 can perform one or more functions described as being performed by another one or more of the devices of environment 200.

UE 210 can include any type computing device, such as a wired or wireless user device, that is capable of communicating with network 250, such as a medical modality. For example, UE 210 can include a smartphone, tablet computer, laptop computer, wearable device, etc. UE 210 can alternatively include a desktop computer, a radiotelephone, a personal communications system (PCS) terminal (e.g., that can combine a cellular radiotelephone with data processing and data communications capabilities), a personal digital assistant (PDA) (e.g., that can include a radiotelephone, a pager, Internet/intranet access, etc.), or another type of computation or communication device. UE 210 can include any variety of peripheral devices, such as speaker, cameras, external storage devices, etc. UE 210 can include a browser or another type of application or interface capable of accessing a DICOM platform hosted by DICOM servers 220.

DICOM servers 220 can include one or more servers or other types of computing devices capable of gathering, processing, searching for, storing, and/or communication information as described herein. In some implementation, DICOM servers 220 can include an application server or a web server that stores one or more applications and/or that permits the one or more applications to be accessed and/or downloaded by UEs 210. DICOM servers 220 can include a single server device, group of server devices, and/or one or more virtual servers. In some implementations, DICOM servers 220 can comprise a DICOM platform as described herein. The DICOM platform can operate, in accordance with DICOM standards, to receive, store, process, secure, and/or provide DICOM information. The DICOM platform can also, or alternatively, include one or more tools, features, or processes capable of perform some or all of the indexing techniques described herein.

In some implementations, DICOM servers 220, in combination with one or more other types of devices, e.g., UEs 210, data repositories 230, platform management terminals 240, etc., can comprise a DICOM platform. In some implementations, DICOM servers 220 can include a vendor neutral achieve (VNA) system capable of receiving and storing DICOM information and other types of data from a variety of sources, such as research instructions, hospitals, doctor offices, etc. In some implementations, DICOM servers 220 can also, or alternatively, be connected to a VNA system and can retrieve DICOM studies and objects from the VNA system for indexing and search processing as described herein.

Data repositories 230 can include one or more data storage devices capable of receiving, storing, and providing data related to DICOM information, the management and processing of DICOM information, etc. In some implementations, data repositories 230 can include a database or another type of data storage system or framework for organizing and storing data. In some implementations, DICOM servers 220 and data repository 230 can be connected via network 250. Platform management terminal 240 can include any type of wired or wireless user device capable of communicating with DICOM servers 220 and/or data repositories 230 via network 250. Platform management terminal 240 can include a smartphone, tablet computer, laptop computer, desktop computer, or another type of user device capable of enabling a user, operator, administrator, or developer to interact with DICOM servers 220 and/or the DICOM platform. In some implementations, platform management terminal 240 can be a UE 210. Additionally, or alternatively, platform management terminal 240 can be directly connected to DICOM servers 220. In some implementations, data repositories 230 can be, or can be part of, a VNA system.

DICOM sources/destinations 250 can include one or more computing devices, such as user devices, network devices, or server device capable of receiving, processing, storing, and communicating information via network 250. DICOM sources/destinations 250 can be owned or operated by a particular institution (e.g., a doctor's office, hospital, research institution, government agency, records archive, etc.). DICOM sources/destinations 250 can be capable of creating and sending DICOM information (e.g., DICOM studies, DICOM objects, etc.) to DICOM servers 220 for processing and/or storage. Additionally, or alternatively, DICOM sources/destinations 250 can request and receive DICOM information from DICOM servers 220 and/or form another DICOM source/destination. In some implementations, DICOM sources/destinations 250 a VNA system capable of receiving, storing, and distributing DICOM information to DICOM servers 220 and/or other DICOM sources/destinations 250.

Network 250 can include a single network or multiple networks capable of enabling a connection between the devices of FIG. 2. Network 250 can include one or more wired and/or wireless networks. For example, network 250 can include a Bluetooth® network, a Wi-Fi network, or a cellular network, the Public Land Mobile Network (PLMN), and/or a second generation (2G) network, a third generation (3G) network, a fourth generation (4G) network, a fifth generation (5G) network, a sixth generation (6G) network and/or another type of network. Additionally, or alternatively, network 250 can include a wide area network (WAN), a metropolitan area network (MAN), an ad hoc network, an intranet, the Internet, a virtual network (e.g., a virtual private network (VPN)), a telephone network (e.g., a Public Switched Telephone Network (PSTN)), a Voice over IP (VOIP) network, and/or a combination of these or other types of networks.

Figure 3:
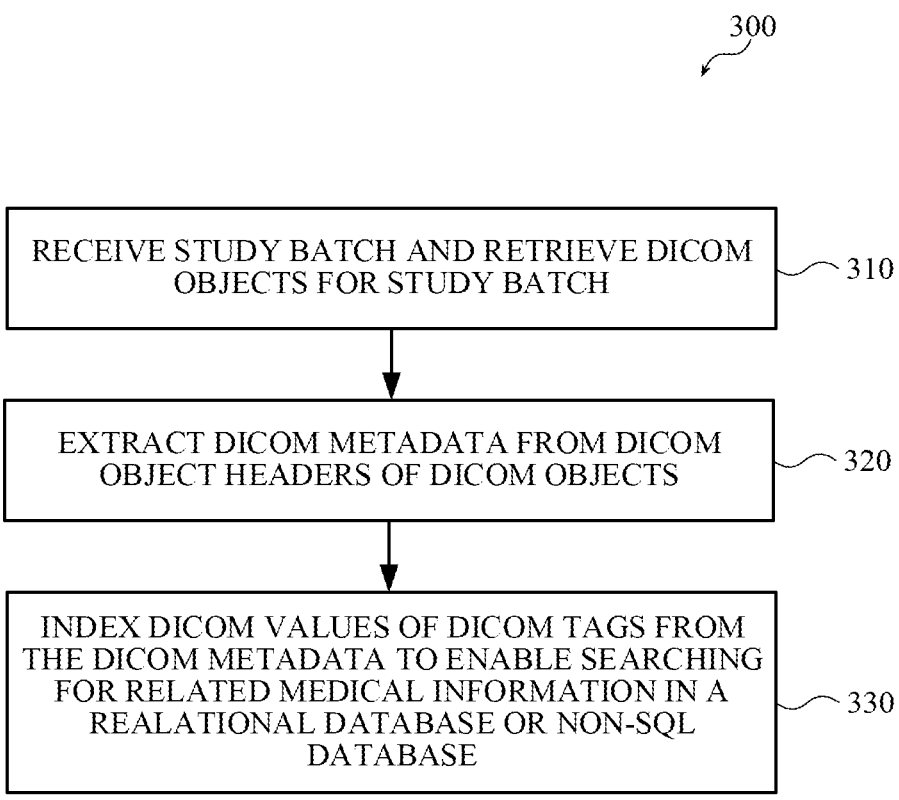
FIG. 3 is a diagram of an example process for indexing DICOM records according to one or more implementations described herein.

FIG. 3 is a diagram of an example process 300 for indexing and searching DICOM records according to one or more aspects or implementations described herein. Process 300 can be implemented by one or more DICOM servers 220. In some implementations, some or all of process 300 can be performed by one or more other systems or devices, including one or more of the devices of FIG. 2. Additionally, process 300 can include one or more fewer, additional, differently ordered and/or arranged operations than those shown in FIG. 3 and can be implemented within the context of a variety of other processes involving different devices. For example, in some implementations, process 300 can include indexing DICOM metadata before searching DICOM records instead or, or in addition to, doing so afterwards.

In some aspects (embodiments/implementations), some or all of the operations of process 300 can be performed independently, successively, simultaneously, etc., of one or more of the other operations of process 300. For example, process 300 can involve include DICOM servers 220 receiving commands or other types of inputs from UE 210, performing one or more operations of process 300, and providing UE 210 with corresponding results or outputs. In some implementations, process 300 can involve include UE 210 requesting and receiving a DICOM study batch from DICOM servers 220, UE 210 indexing certain header tags of the DICOM study batch according and providing the indexed DICOM metadata of the DICOM study batch to DICOM servers 220 and/or to another type of computing device, such as DICOM sources/destinations 250 to enable a relational database or a non-structured queried language (non-SQL) database to be searchable for each value of the DICOM tags.

In some implementations, DICOM sources/destinations 250 can send a request to UE 210 for an anonymized DICOM study batch, UE 210 can communicate with DICOM servers 220 to access (from data repository 230, as a non-SQL or relational database) the DICOM study batch and to properly index each and every value of each tag of each instance of the DICOM study batch and inform DICOM sources/destinations 250 when the indexing is complete so that DICOM sources/destinations 250 can retrieve the indexed DICOM study batch from DICOM servers 220. As such, the techniques described herein are not limited to a number, sequence, arrangement, timing, etc., of the operations or process depicted in FIG. 3 Process 300 is described below with periodic reference to other Figures (FIGs).

As illustrated, process 300 can include receiving a study batch and retrieving DICOM objects for the study batch (block 310). For example, DICOM servers 220 can receive a request from UE 210 to obtain a DICOM study batch (one or more DICOM studies) that includes one or more DICOM objects (also referred to as DICOM records, DICOM instances, etc.). The request for the DICOM study batch can indicate the DICOM objects included in the study. This can be done based on one or more parameters, or combinations of parameters, such as DICOM objects between certain date ranges, associated with a particular hospital or other institution, one or more patient attributes (e.g., name, age, gender, city, state, etc.), one or more type of image data (e.g., x-ray, magnetic resonance imaging (MRI) scan, etc.), one or more DICOM object UIDs, any combination thereof, etc. DICOM servers 220 can retrieve the DICOM objects for the study, based on the request, from data repository 230.

At 320, process 300 can include extracting DICOM metadata from DICOM object headers of one or more DICOM objects of one or more DICOM medical studies. At 330, DICOM values of DICOM tags can be indexed from the DICOM metadata derived from the DICOM object headers to enable medical information of DICOM medical studies to be searchable in a relational database or non-SQL database for each value of the DICOM tags.

At 330, DICOM values of DICOM tags from DICOM metadata extracted can be indexed to enable searching for the medical information in a relational or non-SQL database. In an aspect, indexing the DICOM metadata can include modifying the tags of the DICOM object headers to have an indexable property based on a text based search or an elastic search. A JSON or XML metadata document can be generated based on a DICOM service object pair (SOP) instance unique identifier (SOPInstanceUID) of the DICOM objects. Then a concatenation of the SOPInstanceUID of the metadata can be performed with a tenant domain to index the DICOM values in a DICOM VNA server 220.

Indexing DICOM metadata can include components that create a data processing pipeline. DICOM objects are in binary format. For creating the metadata document, a same starting point as the DICOM web API can be used, in particular the Web Access to DICOM Objects (WADO) request/response (WADO-RS) (DICOM standard) metadata call can be used to initiate the indexing process. The format for the metadata document can be an application for JSON, for example. While this approach can accelerate the final solution metadata generation can be modified or changed, so that an operation is performed to configure the DICOM tag to be an indexable property (or able to be indexed according to the aspects herein). A basic search for the DICOM metadata, for example, can be as follows: "(tag eq dicom_element_tag) and (value eq dicom_element_value), for example a Medical Record Number/Patient ID search could be 0x00100020='MRN200132379'. While the server device/system for indexing generates the slightly modified metadata directly, the processes can be adapted to work with any application that supports the WADO-RS metadata call. An additional process step can be provided to transform the standard metadata format to the indexable format as required. Because the document is in JSON format, a document database is better suited for indexing the metadata document, together with using an Elastic Search as the searching technology (e.g., Apache Solr, etc.) upon which to build on with a simplified language query. However, other search engines that are built on top of a document database and text search technology can be used.

In particular, for batches of DICOM studies or a number of DICOM studies satisfying or exceeding a predefined threshold number of medical studies, metadata can be created from each of the DICOM objects of the batches in response thereto. Whether with batches or individual studies being processed or already archived, nested mappings of the DICOM tags with the DICOM values can be performed to enable correlations to be associated among business keys and value representations of the DICOM tags. The nested mappings can be based on one or more parameters, or combinations of parameters, such as DICOM objects between certain date ranges, associated with a particular hospital or other institution, one or more patient attributes (e.g., name, age, gender, city, state, etc.), one or more type of image data (e.g., x-ray, magnetic resonance imaging (MRI) scan, etc.), one or more DICOM object UIDs, business keys, value representations, or any combination thereof, etc.

Nested mappings of the DICOM tags can be performed with the DICOM values to enable correlations to be associated among business keys and value representations of the DICOM tags. Each value of the DICOM tags of the DICOM object headers comprises a modification with identifying information. The DICOM tags can comprise different value representations including one or more of: a person name, a unique identifier (UID), and short string, a long string, binary data or other tag type, or of the business keys including one or more of: an issuer patient ID and patient ID/medical record number (MRN) at a patient level, a study instance UID at a study level, a series instance UID at a series level, or a DICOM service object pair (SOP) instance unique identifier (SOPInstanceUID) at an instance level. The business keys enable a DICOM study to be assembled from the DICOM object headers at the instance level, from which they can be concatenated with additional identifying information or a nested mapping. In this manner, DICOM object can be configured to be indexable and retrievable in response to a search query based on a RESTful web service endpoint or API operation that interprets the search query string into an Elastic search query. In particular, a simple search query string (a RESTful web service string/or standard search query string) can be interpreted or converted into an Elastic search query string. This can provide a more user friendly analysis of a viewable DICOM study across multiple screens/studies/objects concurrently without interpreting, learning or commanding clastic syntax directly, for example. User friendly terms can be mapped to elastic terms dynamically, which can be configured at the indexing operations or component 120, for example.

A search of the indexed DICOM metadata can retrieve the DICOM objects across studies, series of studies or batches based on the indexed DICOM values to obtain DICOM results of the DICOM objects. The searching can span across one or more DICOM studies based on a variable combination of the DICOM tags that establish an information object hierarchy. The search can be based on a simplified query language associated with a RESTful web service endpoint that is converted into an Elastic search query.

Figure 4:
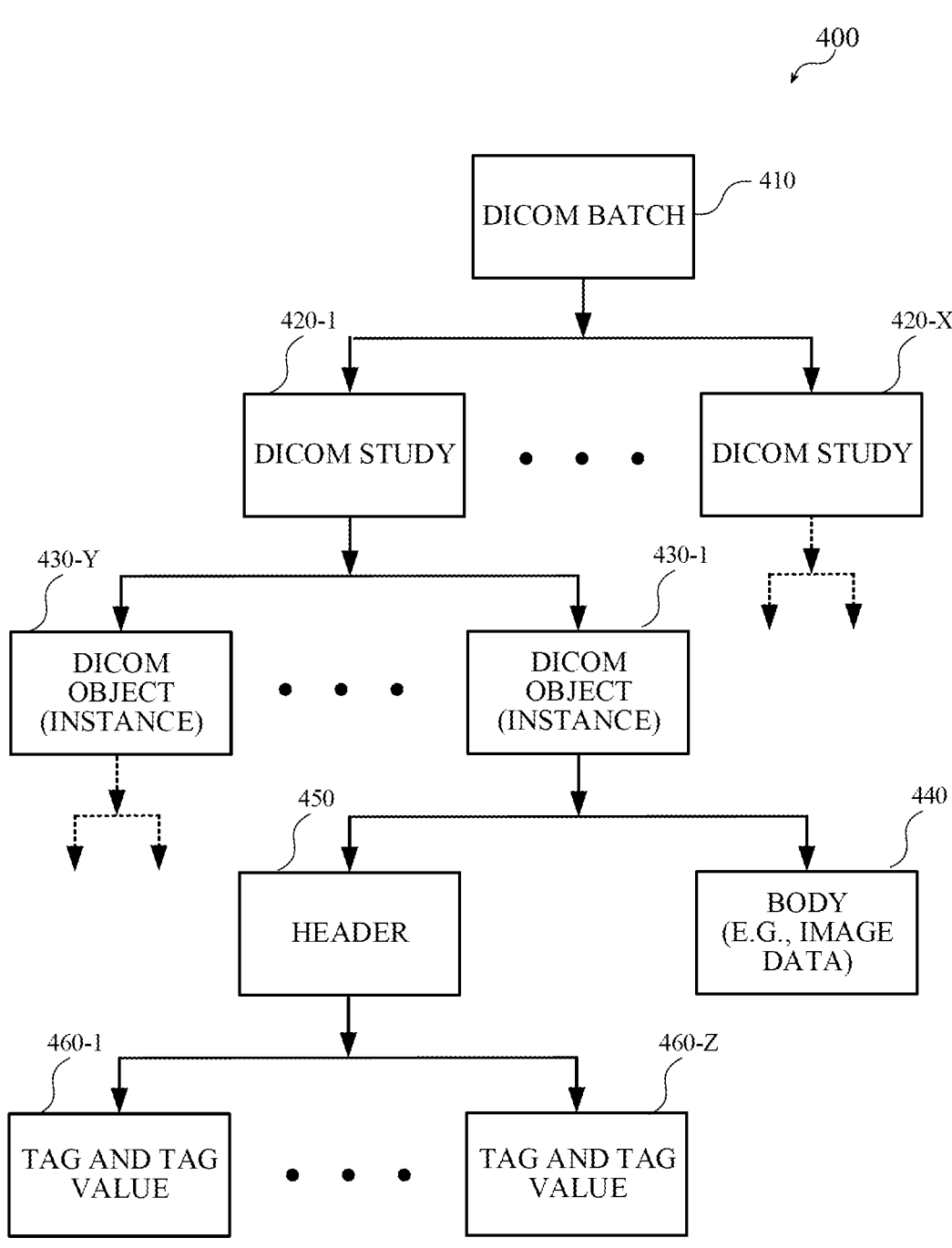
FIG. 4 is a diagram of an example of a data structure of a study batch of DICOM objects according to one or more implementations described herein.

FIG. 4 is a diagram of an example of a data structure 400 at various information entity levels of a study batch of DICOM objects according to one or more implementations described herein. As shown, a DICOM batch 410 can include one or more DICOM studies 420-1, . . . 420-X (where X is greater than or equal to 2) at a study level, and each DICOM study 420 can include one or more DICOM objects 430-1, . . . 430-Y at an instance level, where Y is greater than or equal to 2). A defined number or type of DICOM instances can be considered a series of DICOM instances of a DICOM study, in which a DICOM study has multiple series at the series level. A DICOM study can be associated with a particular patient that can have one or more DICOM studies associated at a patient level. A DICOM object can be referred to as a DICOM instance, and a DICOM object can be implemented as a data file that includes a body 440 (e.g., an x-ray image or another type of image data) and header 450. The header 450 can include multiple tags (also referred to as keys or attributes, including business keys, value representations, or a variable combination of these defining uniqueness at an information entity level for an object hierarchy) and corresponding tag values 460-1, . . . 460-Z (where Z is greater than or equal to 2).

The tags can be specified by the DICOM standards. Examples of tag types can include a patient name, patient age, patient race, patient gender, patient address, patient contact information, patient ID, medical record number (MRN), date when the DICOM object was created, a time when the DICOM object was created, institution where the DICOM object was created, study ID, study instance ID, series instance ID, etc. In some implementations, the values of one or more tags can be a unique identifier (UID). As such, the size of a DICOM batch 410 can vary in size by including one or more DICOM studies 420, which each DICOM study 420 include one or more DICOM objects 430 associated with the study. In some implementations, a DICOM batch 410 can include a single DICOM study 420 and DICOM object 430. In some scenarios, a DICOM batch 410 can include many DICOM studies 420, each with many DICOM objects 430. Techniques, described herein can be used to index and retrieve by search the DICOM batch by, for example, enabling a relational database or a non-SQL database to be searchable for each value of the DICOM tags associated with each DICOM metadata. Each value of a tag of the DICOM object headers can be indexed based on a RESTful web service endpoint and an elastic search, so that the RESTful web service endpoint interprets the search query string into an Elastic search query. Each of the values can be configured with a nested mapping with the various tags. For searches to have 100% matching results the nested mapping can a nested mapping schema of a search index, based a correlation being maintained at the DICOM data element level as a function of one or more tags, value representations (VRs)/type, and a tag value, for example. As a part of the indexing, a Levenshtein distance (string distance) can be configured and associated between a standard DICOM dictionary tag and a query language for performing a search of indexed DICOM values. This can be configured to make the searching via a RESTful search on top of, or in combination with, the elastic search. By associating search query strings with terms within a certain Levenshtein distance a simplified query language can be used that accepts names of tags as defined by a DICOM dictionary to match to a DICOM dictionary tag name in case a query string or search submission is not exact.

Figure 5:
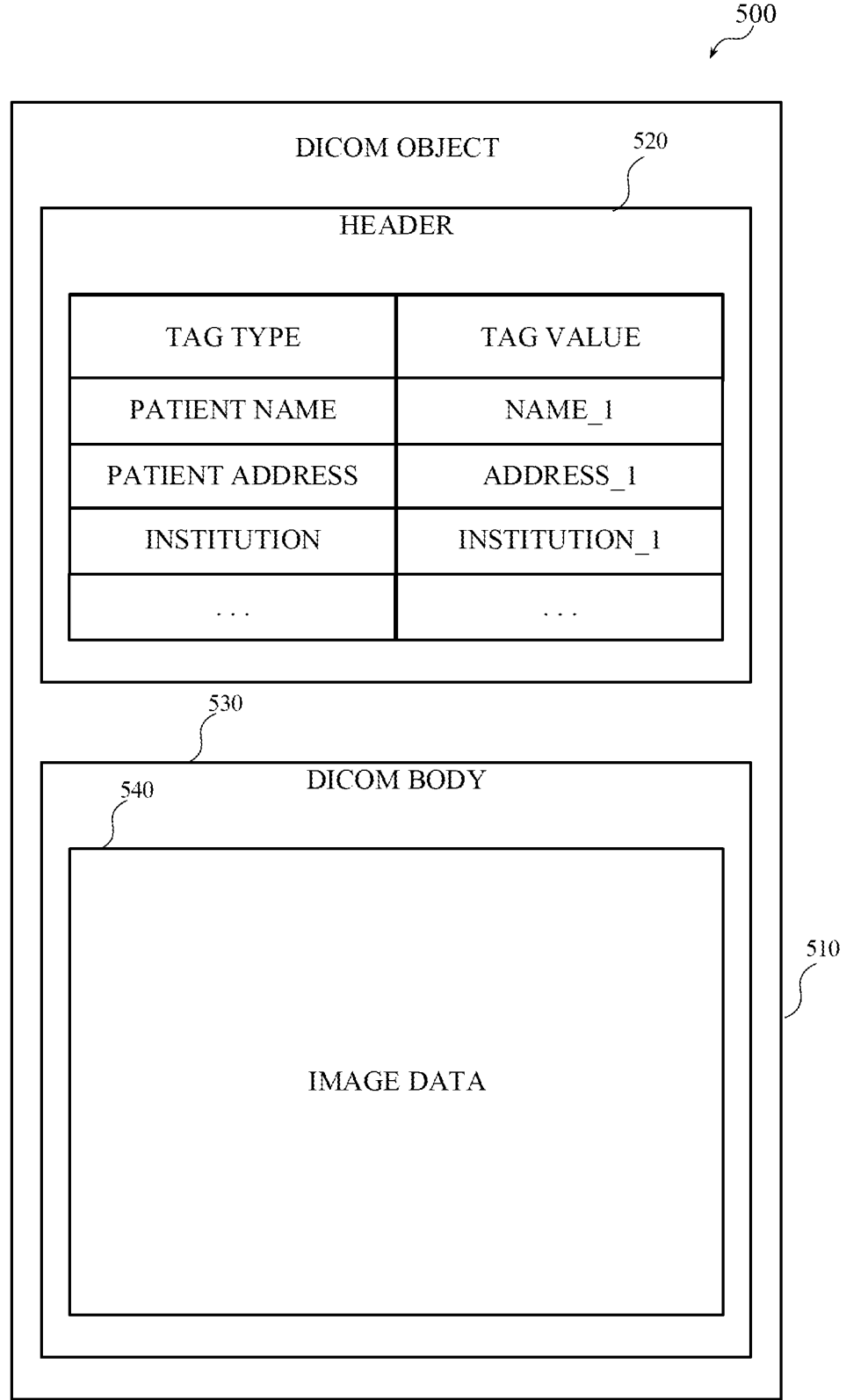
FIG. 5 is a diagram of an example of a DICOM object according to one or more implementations described herein.

FIG. 5 is a diagram of an example 500 of a DICOM object 510 according to one or more implementations described herein. As shown, DICOM object 510 include a header 520 and DICOM body 530. Header 520 can include multiple keys or tags (e.g., patient name, patient address, instruction, etc. Each type of tag can include a corresponding value, such as NAME_1, ADDRESS_1, INSTITUTION_1, etc. DICOM body 530 can include one or more images, or another type of medical information, associated with DICOM object 510. Examples of DICOM body 530 can include image data 540, such as an x-ray image, an MRI, and/or one or more other types of images or medical records, which can also include DICOM metadata with the header information.

Referring to FIG. 3, process 300 can also include indexing DICOM header tag values of DICOM tags of DICOM objects (block 330) by extracting DICOM metadata from each value of every tag of each DICOM header of each DICOM object of one or more DICOM studies. For example, DICOM servers 220 can identify tags in headers of the DICOM objects and index the values corresponding to the tags and their values for every DICOM object header of DICOM objects in a medical study. The extraction can be identified by DICOM servers 220 based on a type, quantity, category, etc., of the DICOM objects, a stated purpose for the record request, a user, institution, or organization indicated as requesting the DICOM study batch, etc. In some implementations, DICOM servers 220 can be configured to extract and index each of the types of header tags, such as identification tags, unique identification tags, etc., for searching and analytics.

DICOM servers 220 can obtain the requested DICOM objects, determine which types of tags or that all types of tags are to be indexed (Block 330), identify the tags in each DICOM object header, and proceed to index the value of the identified tags. This can include DICOM servers 220 using the value of the tag (or a combination or concatenation of the value of several tags) as an input to generate nested mappings of the DICOM tags with the DICOM values to enable correlations to be associated among business keys and value representations of the DICOM tags. In particular, a nested mapping scheme can be performed to ensure a correlation is maintained at a DICOM data element level (e.g., a tag, value representation (VR)/type, and value). For example, search queries producing 100% matching results, can have been defined with nested mappings as part of the processes of the search index, since a correlation is maintained at the DICOM element level. For example, a document search or data search "ds": {"type": "nested", "properties": {"tag": {"type": "keyword"}, "VR": {"type": "keyword"}, "value": {"type": "keyword"}}}.

In an aspect, indexing can include generating XML or JSON metadata documents at the DICOM object/SOPInstanceUID level, rather than DICOM study level with an aggregation of DICOM object headers. The key, value representation used for generating a metadata document can be a concatenation of the SOPInstanceUID and the Domain (Issuer of PatientID/Application Source/Tenant) separated by '-', in which the tenant can refer to the database from among one or more medical enterprises. As such, a text based indexing with or a text indexing engine can be performed on the metadata document or document database with nested mappings to enable elastic searching to be enabled on top of the text based indexing. Because elastic searching can be complex and have a powerful query language, the advantages of both searching can be experienced together. A RESTful web service endpoint can convert simplified query language into an Elastic search query, and thus, provide flexibility with and accuracy of search results that target nested mappings within the metadata indexed. A RESTful search or web service enables services to work best on the web. In the REST architectural style, data and functionality are considered resources and are accessed using Uniform Resource Identifiers (URIs), typically links on the Web, but not always as here. The resources can be acted upon by using a set of simple, well-defined operations. The REST architectural style constrains an architecture to a client/server architecture and is designed to use a stateless communication protocol, typically HTTP. In the REST architecture style, clients and servers exchange representations of resources by using a standardized interface and protocol (e.g., DICOM dictionary terms, or the like). The Elastic search enables a search of the tags as independent values and finds nested mappings that are indexed with various tag or value tag associations based on one or more keys as business keys, value representations or other keys.

Additionally, or alternatively, comprehensive indexing of DICOM metadata can be utilized for very large batches of DICOM studies or DICOM studies exceeding a predefined number threshold. The same analytics request API can be used in order to index a large number of DICOM studies. The metadata of each DICOM object belonging to a DICOM study as part of the batch can be created and then sent to the previously defined (using the nested mappings schema) search index. The API can offer flexibility and more than one index can be used, in case different batches of studies for different analytics purposes are being used. Thus, one mode is to target a specific batch of studies. For example, indexing the metadata of a large batch of studies (e.g., all studies of the year 2022) that are computed tomography (CT) scans of the head anatomy. This may be to focus on one specific area (e.g., head anatomy, or other area) of interest/research. The batch approach where a user uses the API to index a specific batch can save resources. Indexes in Elastic Search or other databases can grow large and use storage space otherwise. The larger the index the more computational resources (CPU) may be needed to run a complex query equally as well.

Additionally, or alternatively, another method of submitting the metadata to the Elastic Search is performing indexing the DICOM instances (e.g., based on DICOM metadata of the DICOM object(s)/object headers) as the DICOM objects are being ingested by the VNA or as the DICOM instances are received by the VNA/archive from the modality or other medical device. In this case, the system or server device basically indexes everything that arrives, although even this could be done programmatically based on rules. As the data comes in or is received, the data can be run through a rules engine to decide whether the data should be indexed or not. The two indexing modes are, explicit specification of the batch where the batch is computed in advance based on specific criteria and the other mode is evaluating if the instance/study is an indexing candidate as the data arrives into the VNA. Both approaches could be used to index the entire VNA. However, rules could be applied to selectively select the DICOM instance candidates.

Figure 6:
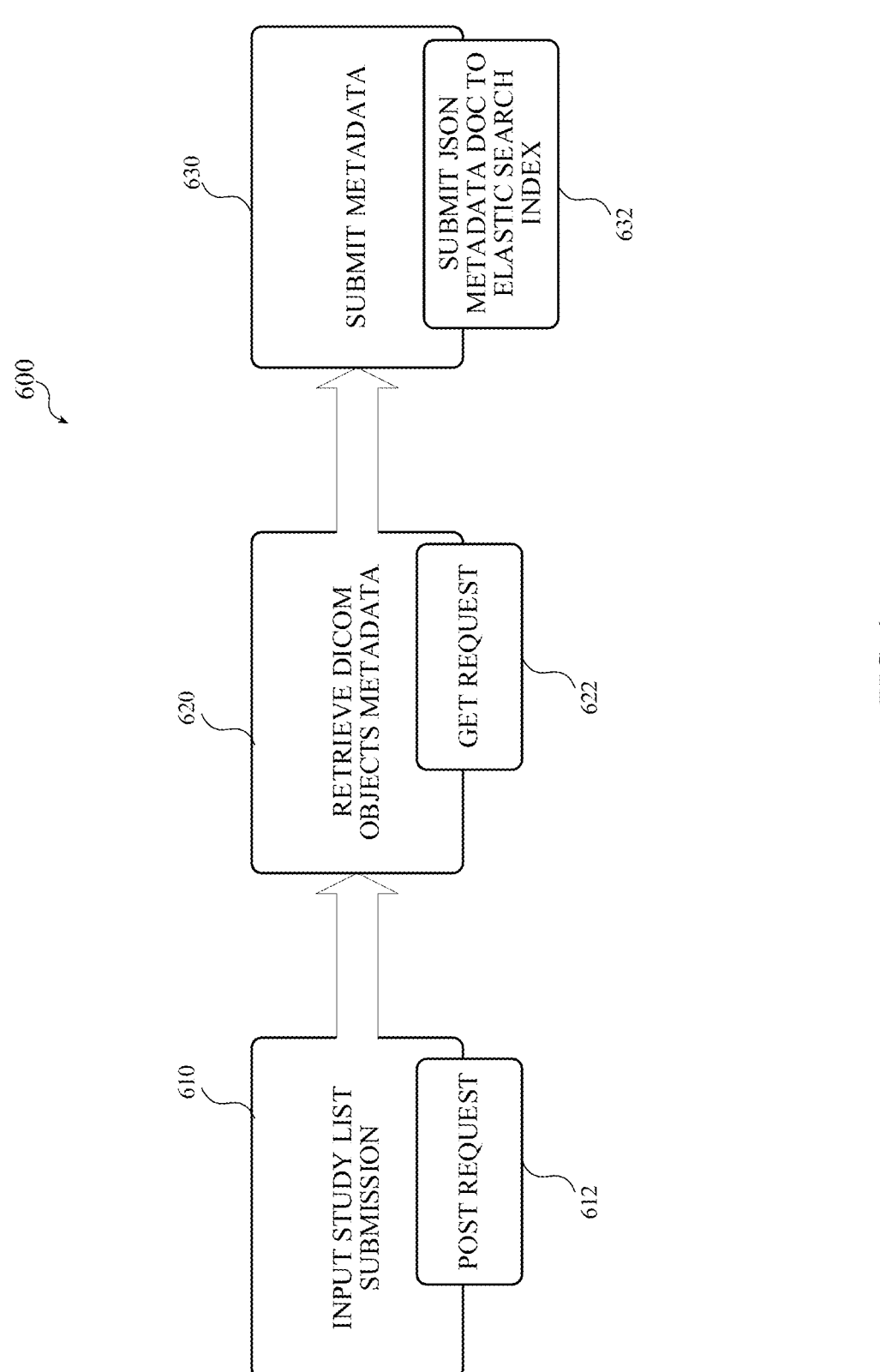
FIG. 6 is a diagram of an example of indexing DICOM metadata of DICOM object header(s) according to one or more implementations described herein.

Referring to FIG. 6, illustrates an example process flow 600 for indexing and searching for DICOM studies. At 610, each DICOM study is inputted (e.g., via a study list submission) or retrieved in a submission set/dataset. This can be performed via a request method support by an html form or http, for example, such as a POST request 612. A POST request is used to send data to a server to create/update a resource. As data comes in for every new study a new index can be sent for. An initial query can be executed for this set, which can be a list of studies to be indexed. The list of studies you can obtained directly out of a DICOM database, or a lightweight query can be executed (e.g., a DICOM C-Find query). For example, all the chest X rays for 2021 may be called for in order for lung studies to be reviewed. So that for each DICOM study in this submission set (the initial list to be processed), the server device can then create a metadata document by extracting each binary representation which is in each header of each DICOM file, to generate a JSON representation. This can then be submitted to this elastic search.

Additionally, or alternatively, at 620, the DICOM metadata of the DICOM objects of the DICOM study can be retrieved (e.g., by a GET request 622). A metadata document can then be created from the DICOM header in a JSON (or XML format). The JSON metadata document can be submitted at 630 to an Elastic Search index by a submit 632 with an ID in the format of the SOP instance UID-Domain as concatenated together as the key used for metadata document.

At this stage all the search capabilities of the Elastic Search technology stack, including visualization capabilities are available to the researcher. While extremely powerful, the search syntax of the Elastic search can be complex, but for sophisticated analysis it may be demanded. To simplify the more common search use cases for the intended user audience, a simplified query language, which is available via a RESTful web service endpoint, can be created by interpreting the query string and then creating the actual Elastic Search query based upon the interpretation. Once the search results are obtained, the results can be aggregated in plain old common language runtime (CLR) objects (POCO) that may be simpler to use by DICOM experts, by aggregating the DICOM object collections into DICOM studies and as discussed above, making clinical actions derived from these search results easy to trigger. For example, a DICOM viewer can be launched based on StudyInstanceUID, or PatientID and Accession Number combination. In radiology, for example, the accession number tag value can be important for interpretation workflows and billing. Other types of tags can include a date, time, date time or study date, for example.

Figure 7:
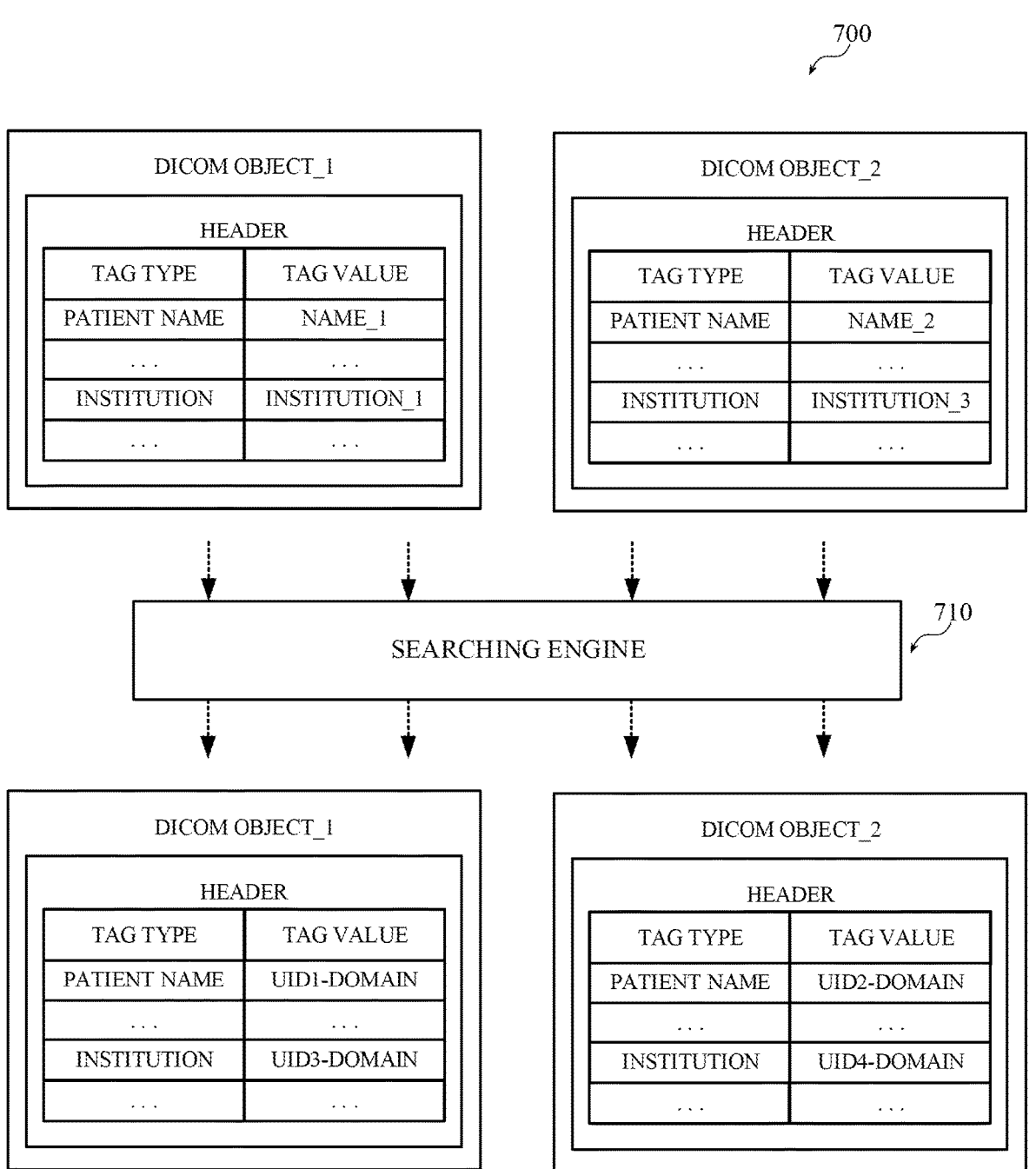
FIG. 7 is a diagram of an example of indexing and searching different DICOM objects according to one or more implementations described herein.

FIG. 7 is a diagram of an example 700 of searching different DICOM objects according to one or more implementations described herein. As shown, DICOM object 1 and DICOM object 2 can each include a header with several tags, such as patient name, institution, etc. DICOM object 1 and DICOM object 2 can also include a body (e.g., an image) though not shown. In example 700, indexing can be used to convert or modify tags or tag values to be indexable based on a text based search or an elastic search. Nested mappings can be generated for the DICOM tags with the DICOM values to enable correlations to be associated among keys including business keys and value representations. Metadata documents are generated based on a DICOM SOP instance UIDs of the DICOM objects concatenated with a domain or tenant domain to index the DICOM values in an VN, such as into various UIDs or UIs, for example. For example, the tag value NAME_1 is converted into UI_1, INSTITUTION_1 is converted into UI_3, and the tag value NAME_2 is converted into UI_2, INSTITU-TION_3 is converted into UI_4. Subsequently, a search can be performed via search engine component 710 based on the indexed DICOM values to obtain DICOM results of the DICOM objects across one or more DICOM studies based on a variable combination of the DICOM tags that establish an information object hierarchy.

Each document with metadata indexed can be at the DICOM instance level. Because of the correlation of the metadata various keys and data for searching can be associated. For example, if all the instances, in which three studies done, one may have been a chest X ray, another a thousand CT studies and then 20 ultrasound studies, which may have all been done over three year, for example, they could all have similar metadata: patient name, MRN if done in the same institution, and then each study have its own ID, or accession number when ordered, which is more human readable but the actual business key as a study instance ID or unique ID. All the instances that belong to the same study can have a same value in order to be correlated. As such, the hierarchy of data can be reconstructed regardless of any user is doing with those objects based on the metadata.

In an aspect, a Levenshtein distance can be calculated based on a hex value of the DICOM tags of an object header from a DICON dictionary. A simplified query language for searching 710 such as a patient ID is 00100020 or the like (e.g., patient birthdate, etc.), can be performed with the submission or query string when not exact. The distance can be used to minimize the rate of failure for searching.

The simplified query language can be a combination of DICOM element tag and DICOM element value, and similarly be converted to an Elastic Search syntax from a RESTful query syntax. In addition to date, time, date time strings, or other interval searches, the searching engine can support wildcards for string values. It also supports more complex expressions composed with operators like conjunction, exclusion, not equal operations or the like (e.g., 'AND', 'OR' and 'NEQ' search operands) to provide results from the DICOM metadata indexing. The tag can be specified as a hex value from the DICOM standard dictionary, for example. However the simplified query language can also accept the names of the tags as defined by the standard DICOM dictionary while computing a Levenshtein distance in trying to find a match to a standard DICOM dictionary tag name string in case the submission is not exact.

In one example, the following example search query string could be submitted at least in part as follow: ((0x00100020 eq 212121) and ((0x00080020 gt 20010101 lte 20050801)). In a search engine, this can cause a DICOM search to find of all DICOM objects that have a PatientID (0x00100020) value of 212121 and a Study Date (0x00080020) between Jan. 1, 2001 and Aug. 1, 2005. In another example, a search query string could be submitted at least in part as follows: (('$Medical Record Number$' eq '212121') OR (0x00080020 gt '20210101' lte '20210801') AND ('$Patient Birth D$' neq '19880111')). This may result in causing a DICOM search to find all DICOM objects that a Patient ID value of 212121, a study date between Jan. 1, 2021 and Aug. 1, 2021 and a Patient Birth Date that doesn't match Jan. 11, 1988. 'Medical Record Number' and 'Patient Birth D' are not tag names in the standard DICOM dictionary. One is a substitution, since MRN, Medical Record Number and PatientID are used interchangeably, the other gets a match via Levenshtein distance, 'PatientBirthDate'.

Various classes that compose the result of a simplified query API can be configured in a search for example. These can include various classes of an Elastic search result, health information technology (HIT) information, a class study info or a series info. The elastic search result can be based on a simple query string, an elastic query string, a tag substitution, or query tag substitution, hit information and a medical study information. The hit information can include a number of studies, a number of instances, and a long Took or long take. The class study information can include a string for a patient ID, a string domain, a StudyInstanceUID, a study date, a series information and the series number. The class series information (SeriesInfo) can include a string for a Series instance UID and string with instances, for example.

Figure 8:
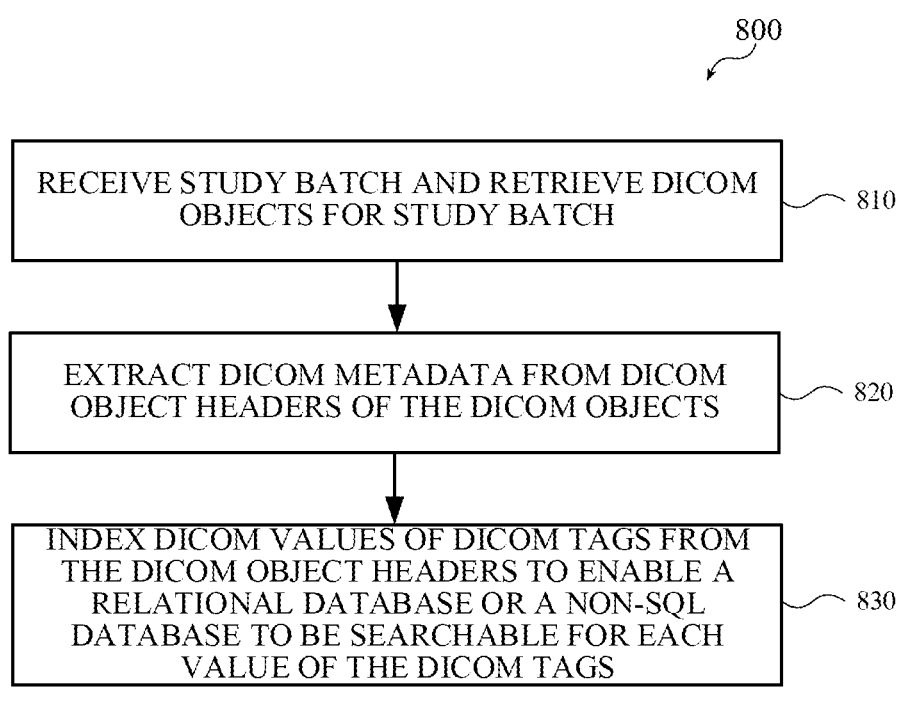
FIG. 8 is a diagram of an example process flow for indexing DICOM metadata of one or more DICOM objects according to one or more implementations described herein.

FIG. 8 is a diagram of an example process 800 for determining how to index and search a batch of DICOM objects based on nested mappings, a Levenshtein distance and a RESTful web service endpoint that interprets a search query string into an Elastic search query to enable powerful indexing and searching in a relational database or a non-SQL database to be searchable for each value of the DICOM tags of DICOM object headers in one or more studies. Process 800 can be implemented by one or more DICOM servers 220. In some implementations, some or all of process 800 can be performed by one or more other systems or devices, including one or more of the devices illustrated in this disclosure. Additionally, process 800 can include one or more fewer, additional, differently ordered and/or arranged operations than those shown in FIG. 8 and can be implemented within the context of a variety of other processes involving different devices. For example, in some implementations, process 800 can include checking for collisions before anonymizing DICOM records instead or, or in addition to, doing so afterwards.

In some implementations, some or all of the operations of process 800 can be performed independently, successively, simultaneously, etc., of one or more of the other operations of process 800. For example, process 800 can involve include DICOM servers 220 receiving commands or other types of inputs from UE 210, performing one or more operations of process 800, and providing UE 210 with corresponding results or outputs. In some implementations, process 800 can involve include UE 210 requesting and receiving a DICOM study batch from DICOM servers 220, UE 210 anonymizing certain header tags of the DICOM study batch and providing the anonymized DICOM study batch to DICOM VNA servers 220 and/or to another type of computing device, such as DICOM sources/destinations 260.

In some implementations, DICOM sources/destinations 260 can send a request to UE 210 for an indexed DICOM study batch in a search or for indexing the study. UE 210 can communicate with DICOM servers 220 to access (from data repository 230) the DICOM study batch and to index the DICOM study batch and inform DICOM sources/destinations 250 when the indexing is complete so that DICOM sources/destinations 260 can retrieve the anonymized DICOM study batch from DICOM servers 220. As such, the techniques described herein are not limited to a number, sequence, arrangement, timing, etc., of the operations or process depicted in FIG. 8.

As shown, process 800 can include receiving a study batch and retrieving DICOM objects for the study batch (block 1010). For example, DICOM servers 220 can receive a request from UE 210 to anonymize a DICOM study batch that includes one or more DICOM objects (also referred to as DICOM records, DICOM instances, etc.). The request for the DICOM study batch can indicate the DICOM objects included in the study. This can be done based on one or more parameters, or combinations of parameters, such as DICOM objects between certain date ranges, associated with a particular hospital or other institution, one or more patient attributes (e.g., name, age, gender, city, state, etc.), one or more type of image data (e.g., x-ray, magnetic resonance imaging (MRI) scan, etc.), one or more DICOM object UIs, etc. DICOM servers 220 can retrieve the DICOM objects for the study, based on the request, from data repository 230.

Process 800 can also include (at block 820) extracting DICOM metadata from DICOM object headers of the DICOM objects.

Process 800 further comprises (at block 830) indexing DICOM values of DICOM tags from the DICOM object headers to enable a relational database or a non-SQL database to be searchable for each value of the DICOM tags. Tags of the DICOM object headers can be modified to be indexable based on a text based search or an elastic search. A JSON metadata document can be generated based on a DICOM SOPInstanceUID of the DICOM objects and a concatenation of the SOPInstanceUID and a tenant domain for indexing the DICOM values in a VNA. Nested mappings of the DICOM tags with the DICOM values can be configured to enable correlations to be associated among business keys and value representations of the DICOM tags. A simplified query language can be associated with a RESTful web service endpoint that is converted into an Elastic search query language. A Levenshtein distance can be computed between a standard DICOM dictionary tag and a query language for performing a search of indexed DICOM values.

A search based on the indexed DICOM values can obtain DICOM results of the DICOM objects across one or more DICOM studies based on a variable combination of the DICOM tags that establish an information object hierarchy. A query string for a simplified search query of the DICOM objects can be interpreted and an elastic search query can be created based on the query string and the Levenshtein distance. The obtained results of the elastic search query can be aggregated in plain old common language runtime (CLR) objects (POCO) for aggregation of the DICOM objects into the one or more DICOM studies and performing clinical actions derived from obtained results of the search query.

Figure 9:
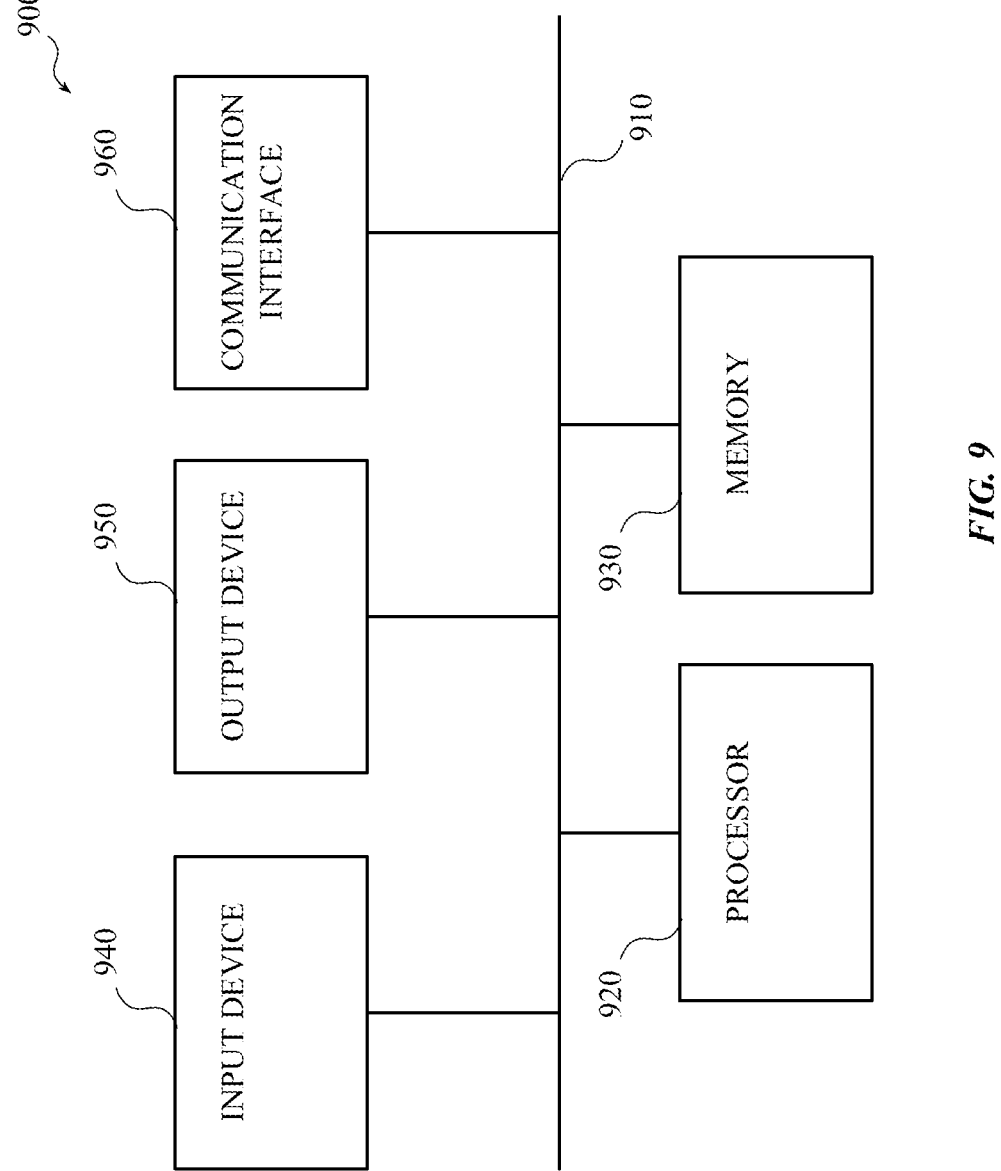
FIG. 9 is a diagram of example components of a device that can be used within environments or implementations (aspects) herein.

FIG. 9 is a diagram of example components of a device 900 that can be used within environment 200 of FIG. 2. Device 900 can correspond to UE 210, DICOM servers 220, data repository 230, platform management terminal 240, and/or DICOM information source/destination 260. Each of UE 210, DICOM servers 220, data repository 230, platform management terminal 240, and/or DICOM information source/destination 260 can include one or more of devices 900 and/or one or more of the components of device 900.

As depicted, device 900 can include bus 910, processor 920, memory 930, input device 940, output device 950, and communication interface 960. However, the precise components of device 900 can vary between implementations. For example, depending on the implementation, device 900 can include fewer components, additional components, different components, or differently arranged components than those illustrated in FIG. 9.

Bus 910 can permit communication among the components of device 900. Processor 920 can include one or more processors, microprocessors, data processors, co-processors, network processors, application-specific integrated circuits (ASICs), controllers, programmable logic devices (PLDs), chipsets, field-programmable gate arrays (FPGAs), or other components that can interpret or execute instructions or data. Processor 920 can control the overall operation, or a portion thereof, of device 900, based on, for example, an operating system (not illustrated), and/or various applications. Processor 920 can access instructions from memory 930, from other components of device 900, or from a source external to device 900 (e.g., a network or another device).

Memory 930 can include memory and/or secondary storage. For example, memory 930 can include random access memory (RAM), dynamic RAM (DRAM), read-only memory (ROM), programmable ROM (PROM), flash memory, or some other type of memory. Memory 930 can include a hard disk (e.g., a magnetic disk, an optical disk, a magneto-optic disk, a solid state disk, etc.) or some other type of computer-readable medium, along with a corresponding drive. A computer-readable medium can be defined as a non-transitory memory device. A memory device can include space within a single physical memory device or spread across multiple physical memory devices.

Input device 940 can include one or more components that permit a user to input information into device 900. For example, input device 940 can include a keypad, a button, a switch, a knob, fingerprint recognition logic, retinal scan logic, a web cam, voice recognition logic, a touchpad, an input port, a microphone, a display, or some other type of input component. Output device 950 can include one or more components that permit device 900 to output information to a user. For example, output device 950 can include a display, light-emitting diodes (LEDs), an output port, a speaker, or some other type of output component.

Communication interface 960 can include one or more components that permit device 900 to communicate with other devices or networks. For example, communication interface 960 can include some type of wireless or wired interface. Communication interface 960 can also include an antenna (or a set of antennas) that permit wireless communication, such as the transmission and reception of radio frequency (RF) signals.

As described herein, device 900 can perform certain operations in response to processor 920 executing software instructions contained in a computer-readable medium, such as memory 930. The software instructions can be read into memory 930 from another computer-readable medium or from another device via communication interface 960. The software instructions contained in memory 930 can cause processor 920 to perform one or more processes described herein. Alternatively, hardwired circuitry can be used in place of, or in combination with, software instructions to implement processes described herein. Thus, implementations described herein are not limited to any specific combination of hardware circuitry and software.

Examples herein can include subject matter such as a method, means for performing acts or blocks of the method, at least one machine-readable medium including executable instructions that, when performed by a machine (e.g., a processor (e.g., processor, etc.) with memory, an application-specific integrated circuit (ASIC), a field programmable gate array (FPGA), or the like) cause the machine to perform acts of the method or of an apparatus or system for concurrent communication using multiple communication technologies according to implementations and examples described.

The above description of illustrated examples, implementations, aspects, etc., of the subject disclosure, including what is described in the Abstract, is not intended to be exhaustive or to limit the disclosed aspects to the precise forms disclosed. While specific examples, implementations, aspects, etc., are described herein for illustrative purposes, various modifications are possible that are considered within the scope of such examples, implementations, aspects, etc., as those skilled in the relevant art can recognize.

In this regard, while the disclosed subject matter has been described in connection with various examples, implementations, aspects, etc., and corresponding Figures, where applicable, it is to be understood that other similar aspects can be used or modifications and additions can be made to the disclosed subject matter for performing the same, similar, alternative, or substitute function of the subject matter without deviating therefrom. Therefore, the disclosed subject matter should not be limited to any single example, implementation, or aspect described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature can have been disclosed with respect to only one of several implementations, such feature can be combined with one or more other features of the other implementations as can be desired and advantageous for any given application.

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Furthermore, to the extent that the terms "including", "includes", "having", "has", "with", or variants thereof are used in either the detailed description or the claims, such terms are intended to be inclusive in a manner similar to the term "comprising." Additionally, in situations wherein one or more numbered items are discussed (e.g., a "first X", a "second X", etc.), in general the one or more numbered items can be distinct, or they can be the same, although in some situations the context can indicate that they are distinct or that they are the same.

It is well understood that the use of personally identifiable information should follow privacy policies and practices that are generally recognized as meeting or exceeding industry or governmental requirements for maintaining the privacy of users. In particular, personally identifiable information data should be managed and handled to minimize risks of unintentional or unauthorized access or use, and the nature of authorized use should be clearly indicated to users.

What is claimed is:

1. A server device, comprising:

a memory; and one or more processors configured, when executing instructions stored in the memory, to:

receive, via an interface communicatively coupled to one or more medical modalities, digital imaging and communications in medicine (DICOM) objects in a DICOM study;

extract DICOM metadata from DICOM object headers of the DICOM objects;

index DICOM values of DICOM tags from the DICOM object headers to enable a relational database or a non-structural queried language (non-SQL) database to be searchable for each value of the DICOM tags; and perform a search based on the indexed DICOM values to obtain DICOM results of the DICOM objects across one or more DICOM studies based on a variable combination of the DICOM tags that establish an information object hierarchy.

2. The server device of claim 1, wherein the one or more processors are further configured to:

modify tags of the DICOM object headers to be indexable based on a text based search or an elastic search.

3. The server device of claim 1, wherein the one or more processors are further configured to:

generate nested mappings of the DICOM tags with the DICOM values to enable correlations to be associated among business keys and value representations of the DICOM tags.

4. The server device of claim 1, wherein the one or more processors are further configured to:

generate a JSON metadata document based on a DICOM service object pair (SOP) instance unique identifier (SOPInstanceUID) of the DICOM objects and a concatenation of the SOPInstanceUID and a tenant domain to index the DICOM values in a virtual network archive (VNA).

5. The server device of claim 1, wherein the search is based on a simplified query language associated with a RESTful web service endpoint that is converted into an Elastic search query.

6. The server device of claim 1, wherein the one or more processors are further configured to:

interpret a query string for a search query of the DICOM objects;

create an elastic search query based on the query string; and aggregate obtained results of the elastic search query in plain old common language runtime (CLR) objects (POCO) for aggregation of the DICOM objects into the one or more DICOM studies and performing clinical actions derived from obtained results of the search query.

7. The server device of claim 1, wherein the one or more processors are further configured to:

receive the DICOM metadata to index from the DICOM object headers; and perform a comprehensive indexing on batches of DICOM studies that satisfy a threshold number of DICOM studies;

create metadata from each DICOM object of the batches of DICOM studies; and send the metadata to one or more previously defined search indices with a nested mapping schema.

8. The server device of claim 1, wherein the one or more processors are further configured to:

compute a Levenshtein distance between a standard DICOM dictionary tag and a query language for performing a search of indexed DICOM values.

9. A method, performed by a server device, comprising:

obtaining, via an interface communicatively coupled to one or more modalities, digital imaging and communications in medicine (DICOM) objects from one or more DICOM studies;

extracting DICOM metadata from DICOM object headers of the DICOM objects;

indexing DICOM values of DICOM tags from the DICOM object headers to enable a relational database or a non-structural queried language (non-SQL) database to be searchable for each value of the DICOM tags; and performing a search based on the indexed DICOM values to obtain DICOM results of the DICOM objects across one or more DICOM studies based on a variable combination of the DICOM tags that establish an information object hierarchy.

10. The method of claim 9, wherein at least a portion of the DICOM objects comprises a header portion and an image portion, the method further comprising: generating JavaScript object notation (JSON) document or an extensible markup language (XML) document from the DICOM metadata.

11. The method of claim 9, further comprising:

generating nested mappings of the DICOM tags with the DICOM values to enable correlations to be associated among business keys and value representations of the DICOM tags, wherein each value of the DICOM tags of the DICOM object headers comprises a modification with identifying information.

12. The method of claim 11, wherein the DICOM tags comprise different value representations including one or more of: a person name, a unique identifier (UID), and short string, a long string, binary data or other tag type, and the business keys including one or more of: an issuer patient ID and patient ID/medical record number (MRN) at a patient level, a study instance UID at a study level, a series instance UID at a series level, or a DICOM service object pair (SOP) instance unique identifier (SOPInstanceUID) at an instance level, wherein the business keys enable a DICOM study to be assembled from the DICOM object headers.

13. The method of claim 12, further comprising:

retrieving an information object hierarchy across a plurality of DICOM studies based on a variable combination of different tags that are modified to be indexable based on the DICOM SOPInstanceUID of the DICOM objects and a concatenation of the DICOM SOPInstanceUID and a tenant domain.

14. The method of claim 9, further comprising:

searching the DICOM tags with the DICOM values based on nested mappings that enable correlations among business keys and value representations of the DICOM tags.

15. A non-transitory computer-readable medium comprising:

instructions that when executed by one or more processors, cause the one or more processors to:

extract digital imaging and communications in medicine (DICOM) metadata from DICOM object headers of DICOM objects of a DICOM study of a medical modality;

index DICOM values of DICOM tags from the DICOM object headers to enable a relational database or a non-structural queried language (non-SQL) database to be searchable for each value of the DICOM tags; and perform a search based on the indexed DICOM values to obtain DICOM results of the DICOM objects across one or more DICOM studies based on a variable combination of the DICOM tags that establish an information object hierarchy.

16. The non-transitory computer-readable medium of claim 15, wherein the one or more processors are further configured to:

retrieve the DICOM objects in response to a search query based on a Restful web service endpoint that interprets a search query string into an Elastic search query string.

17. The non-transitory computer-readable medium of claim 15, wherein the one or more processors are further configured to:

compute a Levenshtein distance between a standard DICOM dictionary tag and a query language for performing a search of indexed DICOM values.

18. The non-transitory computer-readable medium of claim 15, wherein the one or more processors are further configured to:

search the DICOM tags with the DICOM values based on nested mappings that enable correlations among business keys and value representations of the DICOM tags.

19. The non-transitory computer-readable medium of claim 15, wherein the one or more processors are further configured to:

retrieving an information object hierarchy across a plurality of DICOM studies based on a variable combination of different tags that are modified to be indexable based on a DICOM service object pair (SOP) instance unique identifier (SOPInstanceUID) of the DICOM objects and a concatenation of the SOPInstanceUID and a tenant domain.

20. The non-transitory computer-readable medium of claim 15, wherein the one or more processors are further configured to:

receiving the DICOM metadata to index from the DICOM object headers; and perform a comprehensive indexing on batches of DICOM studies that satisfy a threshold number of DICOM studies.

\* \* \* \* \*